(12) United States Patent
Effenhauser

(10) Patent No.: US 6,572,566 B2
(45) Date of Patent: Jun. 3, 2003

(54) SYSTEM FOR DETERMINING ANALYTE CONCENTRATIONS IN BODY FLUIDS

(75) Inventor: Carlo Effenhauser, Weinheim (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 114 days.

(21) Appl. No.: 09/794,464

(22) Filed: Feb. 27, 2001

(65) Prior Publication Data

US 2001/0037099 A1 Nov. 1, 2001

(30) Foreign Application Priority Data

Mar. 3, 2000 (DE) .......................................... 100 10 587

(51) Int. Cl.[7] .............................................. A61B 5/00
(52) U.S. Cl. ...................................... 600/584; 600/365
(58) Field of Search ............................... 600/309, 316, 600/326, 327, 340, 341, 584, 573–575

(56) References Cited

U.S. PATENT DOCUMENTS

| | | | |
|---|---|---|---|
| 4,694,832 A | 9/1987 | Ungerstedt .................. | 128/632 |
| 4,777,953 A | 10/1988 | Ash et al. ................... | 128/635 |
| 4,832,034 A | 5/1989 | Pizziconi et al. ........... | 128/632 |
| 5,097,834 A | 3/1992 | Skrabal ....................... | 128/632 |
| 5,174,291 A | 12/1992 | Schoonen et al. .......... | 128/632 |
| 5,393,401 A | 2/1995 | Knoll .......................... | 204/418 |
| 5,605,152 A | 2/1997 | Slate et al. .................. | 128/634 |
| 5,741,233 A | 4/1998 | Riddle et al. ............... | 604/165 |
| 5,741,284 A | 4/1998 | Karlsson ..................... | 604/160 |
| 5,855,801 A | 1/1999 | Lin et al. ....................... | 216/2 |
| 6,081,736 A | * 6/2000 | Colvin et al. .............. | 600/377 |

FOREIGN PATENT DOCUMENTS

| | | |
|---|---|---|
| DE | 196 02 861 A1 | 7/1997 |
| DE | 196 02 861 C2 | 7/1997 |
| EP | 0 603 154 A2 | 6/1994 |
| WO | WO 95/32416 | 11/1995 |
| WO | WO 97/27475 | 7/1997 |
| WO | WO 98/53739 | 12/1998 |
| WO | WO 99/41606 | 8/1999 |

OTHER PUBLICATIONS

Böhm, S. et al. "A μTAS Based on Microdialysis for on-line Monitoring of Clinically Relevant Substances", Micro Total Analysis Systems 1998, D.J. Harrison, A.v.d. Berg, editor Kluwer Academic Publishers, Dordrecht 1998 (3pp).
Kim, Y. et al. "Needle–Shaped Glucose Sensor with Multi–Cell Electrode Fabricated Surface Micromachining", Part of the Symposium on Design, Test, and Microfabrication of MEMS and MOEMS Paris, France, Mar.–Apr. 1999 (p. 924–930).
Olthius, W. "Various Current Regimes Applicable for Sensing in A μTAS", Micro Total Analysis Systems 98, D.J. Harrison, A van den Berg, Hrsg., Kluwer Academic Publishers, Dordrecht, Boston, London, 1998, (p. 125–128).
Moscone, D.; Venema, K.; Korf, J., "Ultrafiltrate Sampling Device for Continuous Monitoring", Medical & Biological Engineering & Computing, Jul. 1996 (290–294).

* cited by examiner

Primary Examiner—Max F. Hindenburg
Assistant Examiner—Pamela L Wingood
(74) Attorney, Agent, or Firm—Jill L Woodburn

(57) ABSTRACT

The present invention concerns a system for determining the concentration of at least one analyte in a body fluid. The system has a first member and at least a second member of which at least one has a recess on its surface and the members are joined together in such a manner that the recess is closed by a surface of the other member to form a channel. The first and/or second member is composed at least partially of a membrane which is located either in the region of the recess or on the part of the other member that is opposite to the recess such that substances can be taken up from the surrounding fluid by means of the membrane. The system additionally has a sensor which can be used to determine the concentration of an analyte in the channel. Furthermore the system has at least one integrated reservoir which is connected to the channel.

29 Claims, 5 Drawing Sheets

Fig. 1
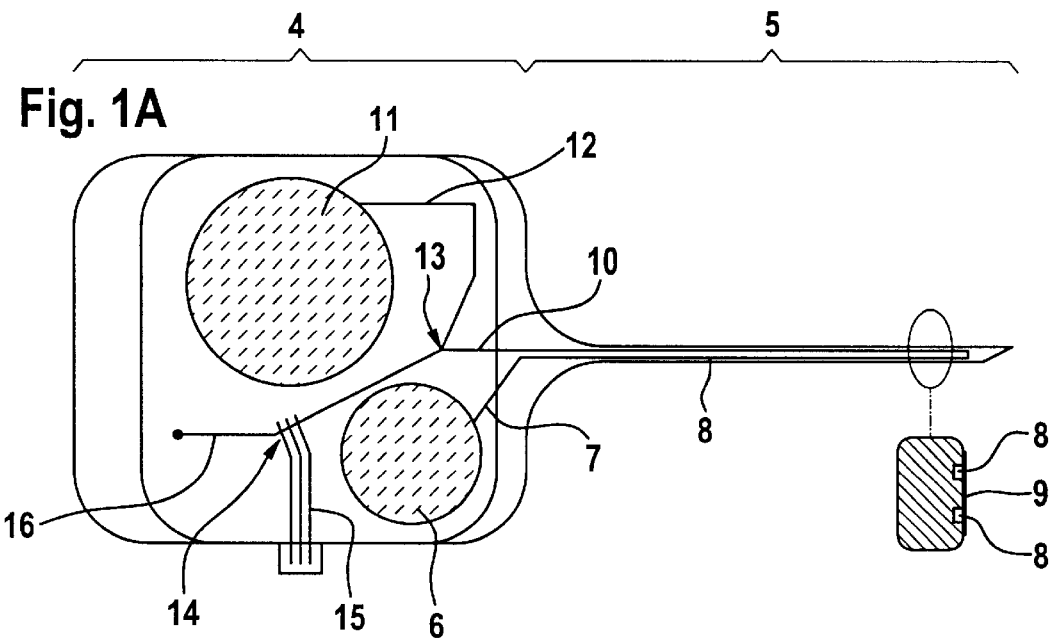
Fig. 1A
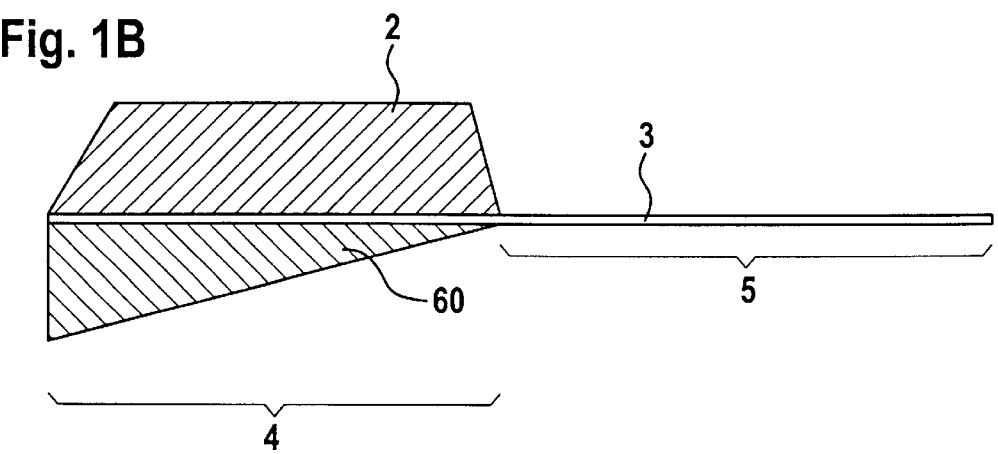
Fig. 1B

Fig. 2
Fig. 2A
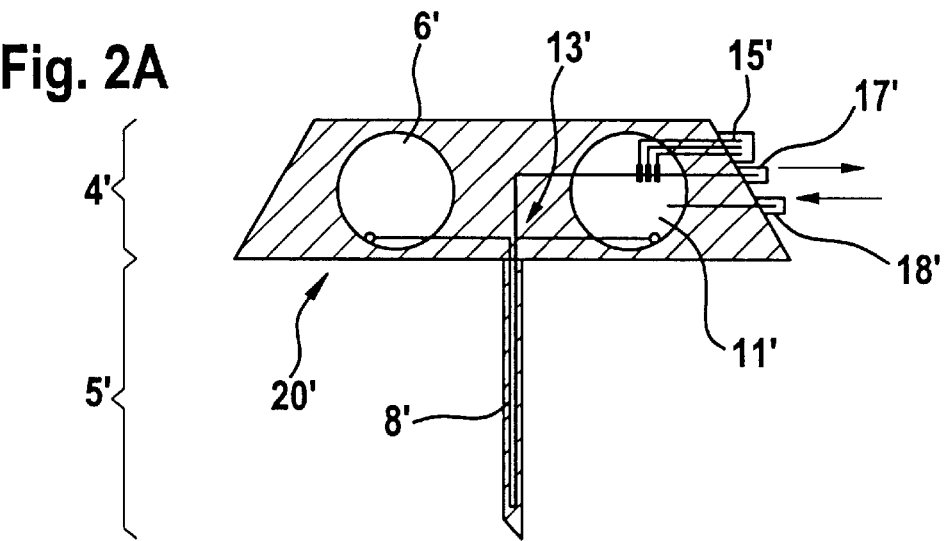
1 cm
Fig. 2B
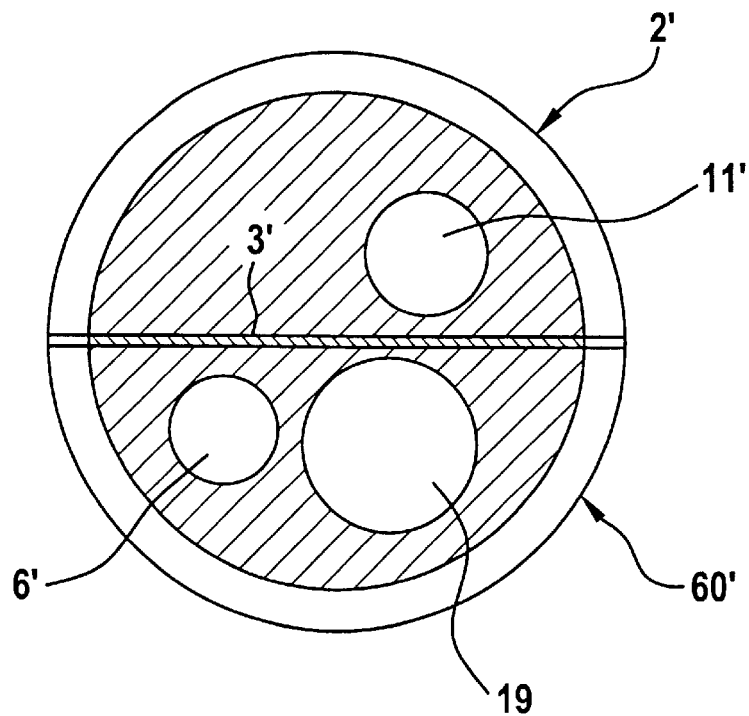

SYSTEM FOR DETERMINING ANALYTE CONCENTRATIONS IN BODY FLUIDS

BACKGROUND OF INVENTION

The present invention concerns a system for determining the concentration of at least one analyte in a fluid, in particular a body fluid. The system has a first member and at least a second member of which at least one has a recess on its surface and the members are joined together in such a manner that the recess is at least partially closed by a surface of the other member to form a channel. The first and/or second member contain an exchange region which is either in the region of the recess or is located on the part of the other member that is opposite to the recess such that substances can be taken up from the surrounding fluid by means of the exchange region. The system additionally has a sensor which can be used to determine the concentration of at least one analyte in the channel. Furthermore the system has at least one integrated reservoir which is connected to the channel.

Many different methods are known in the prior art for the detection of analyte concentrations in body fluids. If the body fluid is extracorporeal, the analyte determination can be carried out in a conventional manner using a clinical analyser. Portable devices such as so-called blood sugar measuring instruments are used predominantly in the prior art for analytes that have to be measured frequently e.g. the glucose content of blood. However, a disadvantage of the said analytical methods is that it is firstly necessary to withdraw a body fluid which usually limits the application range to single measurements. However, in some fields of medicine and especially in the field of diabetes monitoring it is of major advantage to continuously or at least quasi continuously monitor the glucose level. This enables impending hypoglycaemic states which could lead to the death of the patient to be detected in time and, on the other hand, gives a warning of hyperglycaemic states which are usually associated with long-term damage (blindness, gangrene, etc.). Hence recently much effort has been made to enable a continuous monitoring of the blood glucose concentration. One line of research is directed towards a non-invasive measurement of blood glucose concentration e.g. by measuring a glucose-dependent scattering and/or absorbance of infrared radiation. However, up to now it has still not been possible to develop a product based on such a measurement procedure which is ready to go into mass production due to very unfavourable signal to noise ratios and physiological influencing factors that are difficult to control. Other developments are based on the use of sensors that are directly implanted in the body in order to carry out in-situ measurements. A major problem in this technological field is, however, the considerable drift of the sensors that are used. This problem is partially due to the fact that the sensors come into direct contact or via a membrane with tissue and components of the body fluid. Although suitable membranes can reduce this problem, an ageing of the sensor materials takes place which leads to a drift which is very difficult to compensate over a period of several days. Reference is made to the document U.S. Pat. No. 5,855,801 as an example of the above-mentioned technology.

The problems of directly implanted sensors were largely resolved by microdialysis, ultrafiltration and microperfusion. In the case of microdialysis a perfusion liquid is passed through a catheter and the analyte is determined in the dialysate emerging from the catheter. This leads to numerous requirements with respect to liquid handling and microdialysis systems are larger compared to implanted sensors because, among others, perfusate and dialysate have to be stored. On the other hand the microdialysis method is nowadays the most reliable method for monitoring analyte concentrations in vivo.

A number of microdialysis probes are known in the prior art of which reference is herewith made to the arrangements described in the German Patent Application DE 33 42 170 as a representative. The arrangement described in this patent is commercially available under the name CMA 60 microdialysis catheter. This patent shows that a miniaturization of the arrangement is limited by the necessary manufacturing process. However, a reduction in size is absolutely necessary to encourage a more widespread use of the technology. This would be advantageous since smaller microdialysis probes are much lighter and they can be introduced into the body in a less traumatic manner for the patient. Moreover, smaller microdialysis probes can be operated with less liquid so that it is possible to reduce the size of the liquid reservoir.

A miniaturized microdialysis arrangement is described in the article "A $\mu$TAS base on microdialysis for on-line monitoring of clinically relevant substances" S. Böhm, W. Othius, P. Bergveld in: Micro Total Analysis Systems 1998, D. J. Harrison, A.v.d. Berg, editor Kluwer Academic Publishers, Dordrecht 1998. The arrangement has a part manufactured by microtechnology which comprises a sensor and fluid channels and a holding area for the actual microdialysis probe. The described microdialysis probe has an inner channel through which the perfusion liquid flows in and at the end of this channel there is an outer channel through which the perfusion liquid flows out. The microdialysis takes place through the membrane of the outer channel and the dialysate that forms is conveyed to the sensor. Although a relatively large degree of miniaturization has already been achieved with this arrangement, a number of problems remain unsolved. The described arrangement is primarily based on the conventional principle of microdialysis probes composed of concentric tubes in which an inner tube is surrounded by an outer tube which are in fluid communication with one another. This not only results in technical problems for the manufacture but also sets limits for the miniaturization. Furthermore the above-mentioned arrangement is disadvantageous since the microdialysis catheter has to be glued into a holder. This is disadvantageous for the manufacturing process and the junctions between the fluid channels lead to problems. It was found that such fluid junctions impair the response function of the signals. This is due to the fact that the junctions introduce dead volumes.

An solution to the said problems is mostly achieved by systems according to DE 196 02 861. The embodiments described in this document avoid changes in the cross-section of the measuring path and thus circumvent the resulting effects on the response function of the system. Furthermore the described devices allow miniaturization and nevertheless have the advantages of microdialysis described above. DE 196 02 861 also states that it is very easy to integrate sensor elements since the channel is already covered with a membrane that is permeable to the analyte before the sensor elements are inserted. This prevents a closure or contamination of the channel by insertion of the sensor elements. However, this results in a construction that has the disadvantage that the diffusion path for the analyte from the sample liquid is even longer than is already the case for microdialysis. In order to generate a sensor signal the analyte must firstly diffuse through the membrane into the carrier liquid and subsequently out of the carrier fluid through a membrane to the sensor. An additional disadvantage of the systems described in DE 196 02 861 is that the carrier liquid into which the analyte is taken up has to be externally supplied to the sensor system via openings. Connecting tubes in this manner to a miniaturized device not only means additional manufacturing steps but also causes sealing problems. An uncontrolled infiltration of air bubbles into the system is disadvantageous since this would influence the mass transfer in the microdialysis region and also the signal generation in the detection region.

SUMMARY OF INVENTION

The object of the present invention was to propose a miniaturized analytical system which avoids the current problems of the prior art. In particular it was an object of the present invention to propose a system that can be manufactured more efficiently and is capable of being adequately miniaturized. A further object of the invention was to create an integrated system which operates in a largely self-sufficient manner and as far as possible does not need to be connected to external reservoirs. As a result it is possible to omit certain manufacturing steps, the size of the system can be reduced and problems resulting from external connections can be reduced or avoided.

The present object is achieved by a system in which a channel is formed by joining together at least two members, the channel having an exchange area in at least one region such that substances can be taken up from a surrounding liquid/body fluid. In addition the system has at least one integrated reservoir which is connected to the channel.

The system according to the invention is used to determine the concentration of at least one analyte in a liquid/body fluid. Within the scope of the present invention the term "analyte" includes all possible analytes such as glucose, lactate, proteins, electrolytes and neurotransmitters. The term "body fluid" in the sense of the present invention encompasses all possible body fluids and especially interstitial fluid, blood and brain fluid. The system is primarily designed for in-vivo diagnosis in humans, but it can also be used for other applications e.g. for animals.

Within the scope of the present invention the terms dialysis, dialysis membrane etc. are used for embodiments in which an exchange of substances takes place through a membrane between the external space and a perfusion liquid (i.e. microdialysis systems) as well as for systems in which the body fluid surrounding the system is filtered through the membrane (generally referred to as ultrafiltration).

A key aspect of the present invention is the construction of a base member composed of at least two members of which at least one has a recess and the members are assembled such that a channel is formed. This simplifies the manufacture as well as the miniaturization. In particular this integrated construction prevents in a simple manner the occurrence of fluid junctions with cavities, back tapers or such like between the exchange region and the measuring region which would lead to an impairment of the signal. Any fluid junction would, as a result of the manufacture, lead to a region where there is not a direct through flow but which is infiltrated by parts of the main current as a result of edge currents.

The members from which the base member is constructed, in particular the member or members having the recess can for example be manufactured from silicon by known methods for microprocessing silicon. However, for manufacturing cost reasons it is preferred to manufacture the members from plastics, metals or ceramics. In particular the member or members can be manufactured in a simple and cost-effective manner from polymers in an injection moulding process in which for example recesses can be directly introduced in the base member for the reservoirs and channels during the injection moulding process. It is also possible to subsequently process a plastic member by stamping techniques. Plastics which can be used for this purpose are for example polymethylmethacrylate and polycarbonate. However, embodiments should also be included in which a coating is subsequently applied to the base member. This may be advantageous or necessary in order to passivate the surface, to give it a suitable surface tension or to attach electrodes. Methods for applying such coats are for example to vapour deposit or sputter metals such as gold, silver and aluminium. Since these methods are well-known in the prior art they are not elucidated in more detail here.

The base member has an exchange region through which the substances from the surrounding body fluid can be taken up into the channel. This uptake can be achieved by passing a liquid (perfusion liquid) over a membrane (i.e. microdialysis) or by taking up liquid into the channel through a membrane (ultrafiltration) by applying a pressure gradient. Furthermore it is also possible to provide perforations in the exchange region through which substances can be taken up from the external space. Such a procedure is usually referred to as microperfusion.

A special feature of the present invention is that the exchange region is not formed by a system of coaxial tubes as is commonplace in the prior art as described for example in DE 33 42 170, but instead the exchange region is formed by a channel in the base member which is open at the top and is covered by a membrane or a perforated region. If perfusion liquid is passed through the channel while the exchange region is in contact with the body fluid, the perfusion liquid takes up substances from the body fluid.

In the case of microdialysis and ultrafiltration the type of substances that can be taken up depends on the properties of the membrane and especially its pore size. It is basically possible to use the materials that are used in the prior art for the membrane such as polycarbonate, cellulose acetate, polysulfone. A description of suitable membranes is given for example in DE 196 02 861 and U.S. Pat. No. 4,832,034.

The main purpose of the membrane is to exclude molecular substances which interfere with the analysis or age the sensor. Consequently substances with a molecular weight of >10,000 Daltons should be excluded by the membrane.

In the case of microperfusion the exchange region has perforations through which fluid can be exchanged directly between the external space and the channel. The individual perforations can have an opening cross-section from a few micrometers up to about 0.5 mm. With regard to the procedure for microperfusion reference is made here to the document U.S. Pat. No. 5,097,834.

Whereas conventional microdialysis catheters have an exchange surface having an essentially cylindrical shape, the exchange region of the present invention has an essentially planar surface above the channel as the exchange surface. This reduced exchange surface on an absolute scale is compensated by the fact that the channel can be designed to be very small and in particular flat in the exchange area which leads to a favourable surface/volume ratio and ensures a rapid percentage concentration with analyte. Conventional microdialysis probes have an active catheter length in the range of a few centimeters. The exchange region according to the present invention allows lengths of 1 cm and less. If the channel has an appropriate shape in the exchange region such as loops or meanders the required length of the member can be further reduced and the active length enlarged. As already stated an exchange region is created in the present invention by covering a channel with a membrane or a perforated structure in the dialysis region. For this purpose the membrane or the perforated structure can be for example glued onto or sealed onto the dialysis region.

The exchange region of the base member preferably has an elongate shape such that it has the shape of a rod. The rod is preferably connected monolithically with the base member (or with a member of the base member). Part of the rod that is connected to the base member is referred to as the proximal end, whereas the opposite end is referred to as the distal end. The distal end can for example be pointed to facilitate insertion into the body. On the other hand it is not necessary to have a tip when a so-called introducer device is used to insert the dialysis region into the body. Numerous different types of introducer devices exist in the prior art which are not elucidated in more detail here. Reference is merely made to the documents WO 97/14468 (TFX Medical Inc.) and WO 95/20991 (CMA Microdialysis Holding AB) as representative examples.

The channel in the exchange region is designed to have an inlet and an outlet which are both preferably located on the proximal end of the dialysis region. In this connection it should be mentioned that it is hardly possible to strictly differentiate between the channel of the exchange region (exchange channel) and the other channels of the base member since these channels merge into one another. However, it is possible to define the exchange channel as referring to that part of the channel that is covered by the dialysis membrane or by the perforated structure and thus contributes to the exchange process. Liquid which emerges from the exchange channel can be conveyed directly or via a channel to the measuring region on the base member. In order to reduce the time lag between uptake of the measured value i.e. the exchange process and the measurement, the channel is usually chosen to be as short as possible. The channel is in turn formed by a channel in the base member which is open at the top and which is covered by a cover plate. This cover plate can in principle be made of the same material as the base member and in particular of plastics. The term "cover plate" is also intended to include those embodiments which in everyday usage are more likely to be referred to as a foil due to their low thickness. The cover plate should be composed of a liquid-impermeable material and it usually does not have to meet other special requirements. It should also be mentioned that a material should be selected which is compatible with the dialysate or microperfusate and does not lead to any changes which could affect the concentration of the analyte to be determined or the analysis as such. For certain analytes it may, however, be advantageous when the cover plate or at least a part thereof in the region of the channel is permeable to air. This is particularly advantageous for the detection of glucose by means of glucose oxidase since glucose is usually oxidized with atmospheric oxygen for its detection. In such a case it is advantageous to already saturate the perfusion liquid with oxygen. For this purpose the cover plate can be completely or partially manufactured from a material that is permeable to oxygen e.g. a silicon.

At least one sensor is located in the measuring region of the base member in order to detect an analyte. A metal electrode can for example be used to detect glucose the surface of which is coated with glucose oxidase or with a reagent mixture containing glucose oxidase. This electrode is preferably located on the cover plate in such a manner that it is positioned in the measuring region above the channel and downstream of the exchange region when the cover plate and base member are joined together. Such an electrode can for example be mounted on the cover plate by vapour depositing or sputtering a metal strip which is subsequently coated with glucose oxidase or a reagent mixture. Screen printing processes are for example suitable for applying reagent mixtures on electrodes. However, the electrode can in principle also be mounted on the base member as a separate component.

In addition to the described measuring electrode, the system also has a counterelectrode which can be mounted on the cover plate in a corresponding manner. In an arrangement which is described below in more detail, it is possible to omit the coating of an electrode with a reagent mixture since a liquid solution of glucose oxidase is mixed with the dialysate. This measurement procedure and a suitable sensor arrangement for this is described in EP B 0 393 054. In addition to the aforementioned electrical measuring cells, it is also possible to use optical measuring cells within the scope of the present invention. For this purpose a reagent system that forms a colour with the analyte can for example be located in the measuring region as is known for test strips for blood glucose measurement. An optical sensor that is suitable for measuring the glucose concentration is described for example in EP A 0 693 271. Another possibility of providing the system with a sensor is to use the measuring cells according to U.S. Pat. No. 5,393,401. These measuring cells can be integrated into the base member either as separate components or by introducing a recess in the member which tapers towards the channel in which the sensor system is located.

An essential aspect of a system according to the invention is that although fluids are transported to enable a detection as is the case with microdialysis, ultrafiltration and microperfusion, the liquids that are necessary for this or the reservoirs for holding liquids are integrated as far as possible, preferably completely, into the base member so that connections for liquids can be omitted. This is achieved by integrating reservoirs into the base member. For carrying out a microdialysis, it is for example advantageous to provide a reservoir for the perfusion liquid and/or a reservoir for receiving the dialysate after the analysis. In the case of an ultrafiltration in which perfusion liquid is not normally used, a waste reservoir can be provided according to the invention downstream of the measuring position in order to receive ultrafiltrate. For a microdialysis as well as for an ultrafiltration it may be necessary or advantageous to use auxiliary fluids such as enzyme solutions (in particular glucose oxidase solution) or calibration liquid. Reservoirs for holding these auxiliary liquids can also advantageously be integrated into the base member. In this connection any inlet channel in the base member that can be avoided is an advantage since this allows omission of the corresponding working steps for connection, manufacture and sterilization and avoids problems with fluid junctions such as leak-proofness and signal impairment.

In a particularly preferred system all necessary reservoirs are integrated into the base member so that it is possible to completely omit external connections for fluids. Such a system has a closed liquid path.

A system according to the present invention, if it is used to carry out a microdialysis or a microperfusion, has a reservoir for the perfusion liquid which is connected directly or via a perfusate channel to the exchange region. The reservoir for the perfusion liquid and optionally the perfusate channel are integrated into the base member. However, embodiments are also possible in which the reservoir is present separate from the base member for example in the form of a plastic bag which is connected directly or via a channel to the exchange region. However, due to the above-mentioned manufacturing problems of discretely constructed systems, it is advantageous to provide a reservoir for the perfusion liquid in the base member. This can be achieved by a recess in a member which is closed by being covered with an additional member. In this connection it should also be mentioned that the present invention also encompasses the use of two or more discrete members, for example plates, instead of a single member to cover the first member. This may be advantageous when it is intended to close the reservoir and cover the measuring region in separate steps.

A pump is provided according to the invention to transport perfusion liquid through the exchange region and to the sensor region. Such a pump can for example be pressure operated and press liquid out of the reservoir for the perfusion liquid or it can also be suction operated and pull liquid through the system. In addition a pump can for example be disposed such that it draws out liquid from the fluid reservoir and transports it to the exchange region. The latter variant can be designed like a conventional peristaltic pump in which an externally applied roller element pushes liquid by squeezing a compressible region of the fluid channel. Such a compressible part can for example be realised in the region of the perfusate channel when one of the members is designed to be deformable in this region.

A pressure pump can be realised within the scope of the present invention in that the system is designed to be compressible in the region of the perfusate reservoir and by applying mechanical pressure on this region from outside. In addition it is possible to apply gas pressure to the interior of the perfusate reservoir in order to press out perfusion liquid. Corresponding systems are for example common in the field of implanted delivery devices. However, reference is made by way of example to the document WO 99/41606 (FIG. 7) from the field of microdialysis.

As already mentioned suction pumps can also be used within the scope of the present invention which are used to apply underpressure downstream of the measuring region in order to pull liquid through the exchange region into the sensor region. Suitable suction systems are for example known from the field of on-line monitoring of body fluids by means of ultrafiltration. In particular reference is made in this connection to the systems described in the article "Ultrafiltrate sampling device for continuous monitoring"; D. Muskone, K. Venema, J. Korff; in Medical a. biological engineering and computing, 1996, 34, pages 290–294, and in U.S. Pat. No. 4,777,953.

In these systems an underpressure reservoir is firstly created e.g. by drawing up a syringe and the filling of the underpressure reservoir is delayed by a flow restriction such that an essentially constant flow is achieved over a period of several days.

Channels with a diameter in the range of 10–1000 $\mu$m are preferably used for the present invention. In the case of channel lengths that are in the range of a few centimeters, this means that pressures in the range of a few millibar are sufficient to achieve linear flow rates of about 1 cm/min. However, this also means that even slight pressure variations (e.g. changes in the position of the system) may have an unintentional effect on the liquid transport. Correspondingly it is advantageous within the scope of the present invention to incorporate flow restrictions which have the effect that liquid transport does not occur until a relatively large pressure difference is present. Such flow restrictions can be advantageously integrated in the base member by providing channel regions in which the cross-section of the channel is reduced (for example below 100 $\mu m^2$) over a length of several centimeters. Such reductions in cross-section can be simply achieved using the production techniques for base members that are described above.

A system according to the invention also has an analytical unit connected to the sensor which serves to convert sensor signals into concentration values for the analyte. Such analytical units are well-known in the prior art for example for electrochemical blood sugar measuring instruments so that they do not have to be described in more detail here. However, it should be noted that the analytical unit does not need to be directly connected to the sensor but that for example a transmitter can be provided which is connected to the sensor and transmits signals to a receiver which is in turn connected to an analytical unit. Such a spatial separation between the base member and the analytical unit can be advantageous for several reasons. On the one hand this frees the system of ballast (analytical unit, display). In particular it makes the system more comfortable to be carried by a patient.

BRIEF DESCRIPTION OF DRAWINGS

The present invention is further elucidated on the basis of some figures.

FIG. 2: Top-view (FIG. 2A) of and vertical section (FIG. 2B) through a base member of a second embodiment of a microdialysis system.

DETAILED DESCRIPTION OF DRAWINGS

Figure 1C:
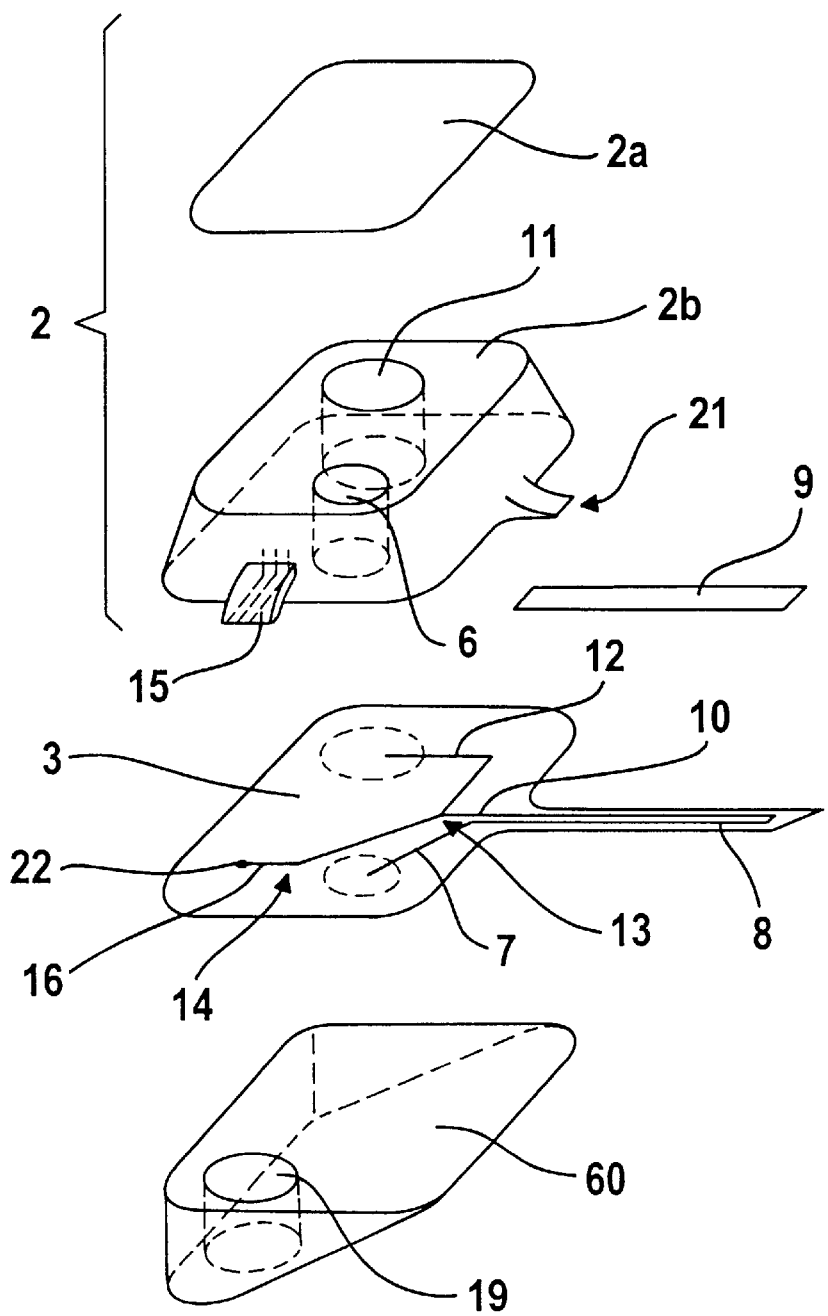
FIG. 1: Top-view (FIG. 1A), vertical section through the base member (FIG. 1B) and exploded diagram of a first embodiment (FIG. 1C).

FIG. 1 shows a first embodiment of a base member for a microdialysis system. FIG. 1A shows that the base member has two regions. The first region (4) contains the measuring region and the second part (5) contains the dialysis region. In the embodiment that is shown there is a recess in the first region (4) in a first member (upper part, 2) which forms a reservoir (6) for the perfusion liquid when it is joined together with a second member (3). In the present case the reservoir has a volume of 250 $\mu$l and contains Ringer's solution which is common in the field of microdialysis. Perfusion liquid can be pressed out of this reservoir through the perfusate channel (7) into the dialysis channel (8) by applying a pressure. In the example shown the dialysis channel (8) consists of a recess in the dialysis region of the second member which is open at the top. This channel extends from the proximal end of the dialysis channel to the vicinity of the distal end where it bends and runs back into the proximal part of the dialysis region. The sectional diagram which shows a cross-section through the front part of the dialysis region shows that the channel (8) is covered by a membrane (9) which enables a dialysis when the dialysis region is in contact with a body fluid. The membrane can preferably extend beyond this region and cover the entire upper side of the second member. This avoids sealing problems at the seam between the first member—second member—membrane. Recesses or perforations can be provided in the membrane in order to provide access to the sensors and reservoirs.

The outlet of the dialysis channel is connected in the first region (4) to the dialysate channel (10) through which the dialysate formed in the dialysis region is transported into the measuring region (14). A sensor (15) is located in the measuring region which can be used to determine an analyte concentration in the dialysate. A sensor that is suitable for this purpose is described for example in EP B 0 603 154 (AVL Medical Instruments AG). In contrast in the case shown in the figure a simple metal electrode sensor is used as described in EP B 0 393 054. This sensor operates without an immobilized enzyme thus avoiding problems that otherwise often occur such as signal drift. When this sensor is used, a solution of glucose oxidase is admixed in the present case with the dialysate such that glucose is oxidized in the liquid to form hydrogen peroxide. The hydrogen peroxide is the actual agent which is detected by the sensor. The solution of glucose oxidase can for example be used as a perfusion liquid so that the microdialysis arrangement only needs one liquid component. However, in order to completely prevent the escape of liquid containing glucose oxidase into the body of a patient, it is preferable to mix the glucose oxidase solution with the dialysate that has already formed as shown in FIG. 1. A mixing position (13) is provided for this purpose in FIG. 1. The region of the dialysate channel downstream of the mixing position (13) can advantageously be covered by a material that is permeable to oxygen so that the oxygen-consuming oxidation of glucose can proceed to completion. After the dialysate has flowed past the measuring region (14) it passes into a waste channel (16) and is passed from there into a waste reservoir (19) which is located in the bottom part (60). The centimeter scale shown in FIG. 1 shows the extent to which the microdialysis system can be miniaturized by using an integrated base member.

FIG. B shows a cross-section through the base member. The reservoirs (6, 11) shown in FIG. A are located in the upper part (2). The second member (3) has recesses which form a channel system when it is sealed with the upper part. The second member also has a through bore which is in fluid connection with the waste reservoir of the lower part (60, third member) such that a reservoir is formed when the second and third member are joined together. There are hardly any limits to the outer geometric shape of the dialysis region and of the lower part and hence they can be adapted to anatomic requirements.

FIG. 1C shows an exploded diagram of the microdialysis system. This representation shows that the upper part (2) can in turn advantageously consists of two parts (2a, 2b). The lower part (2b) has bores which form reservoirs for the perfusion liquid (6) and for glucose oxidase solution (11) in conjunction with the upper part (2a) and the second member (3). In addition the part (2b) supports electrodes (15) on its lower side which form the measuring cell. In order to make a liquid-tight connection, the part (2b) additionally has a lug (21) which rests above the membrane (9) in the assembled state. FIG. 1C additionally shows the microstructure of the second member (3) with grooves disposed on its surface which in conjunction with part (2b) provide the channels (7, 8, 10, 12, 16). The member (3) additionally has a through bore through which the liquid passes from the channel (16) into the waste reservoir (19). In order to transport fluid in the microdialysis system, an underpressure can be applied to the waste reservoir such that liquid is pulled from the reservoirs (6, 11) through the channels. The flow rate can be adjusted by the resistance to flow of the channel system and in particular by the channel cross-sections.

FIG. 2 shows a base member of a second embodiment that is constructed analogously to the embodiment shown in FIG. 1. Reference numerals which correspond to those of FIG. 1 are the used for the individual units and they are distinguished by prime symbols. An important difference between the two embodiments is that the construction of the second embodiment has been selected such that the dialysis region (5') can be inserted perpendicularly into the body and the surface (20') of the first part of the base member (4') rests on the body. The liquid transport takes place in the arrangement shown in FIG. 2 analogously to that of FIG. 1 in that perfusion liquid passes from the reservoir (6') through the dialysis channel (8'), glucose oxidase solution from the reservoir (11') is mixed with it at the mixing position (13') and finally it reaches the sensor (15'). In this embodiment the liquid transport is achieved by applying underpressure to the connection (17') such that liquid is transported from the reservoir (6') through the dialysis channel and to the sensor. The amount of added glucose oxidase solution can be regulated by regulating the inflow of liquid or air into the reservoir (11') through the inlet (18').

FIG. 2B shows a top-view. It can be seen that the region 4' is composed of two halves between which a plate (3') is located. The plate (3', second member) has recesses which form fluid channels together with the one half (first member; 2') and/or the other half (third member, 60'). The structuring on both sides of the plate (3') enables numerous channel geometries (3') to be realised. The two-sided structuring in the exchange region also enables an enlargement of the exchange surface. FIG. 2B also shows a waste container (19) which is located downstream of the sensor.

Figure 3:
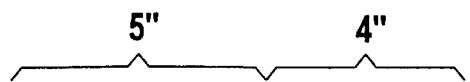
FIG. 3: Diagram of various layer combinations for generating the base member (FIGS. 3A–3C).
Figure 3A:
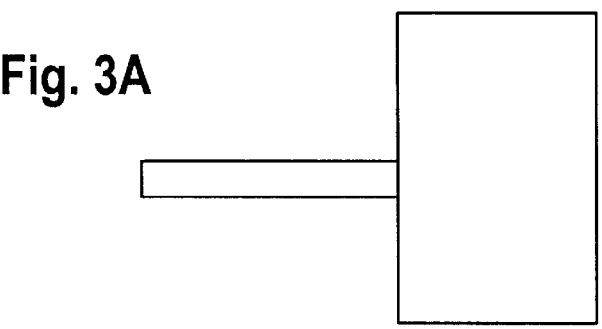
Figure 3B:
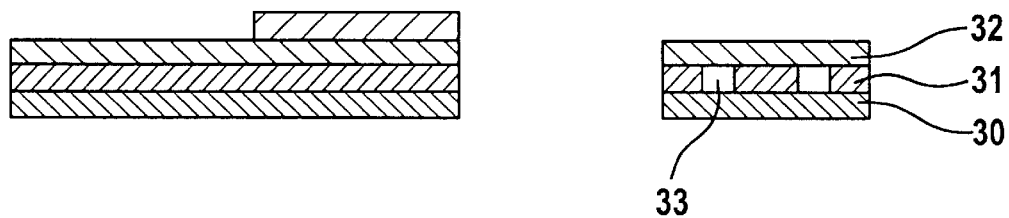
Figure 3C:
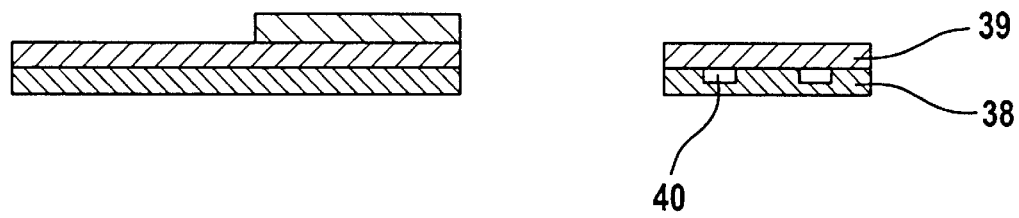

FIG. 3 shows a system according to the invention which is composed of several layers. As shown in FIG. 3A this system also has an exchange region (5") for insertion into the body and a region (4") in which the measuring region is located. FIGS. 3B–3C show cross-sections along the exchange region (left column) and at right angles through the exchange region (right column). These figures show different layer structures for making the channels. In FIG. 3B an unstructured plate (30) with a planar surface has firstly been used on which a plate (31) with recesses is mounted. Both plates acting together result in a first member which has channels on its surface that are open at the top. This channel or channels are covered in the present case by a membrane (32) to form a closed channel (33).

FIG. 3C finally shows an embodiment in which a member (38) with a surface structure having recesses that are open at the top has been used which is covered by a flat membrane (39). In this case interaction between the members results in one or several fluid channels (40).

Figure 4:
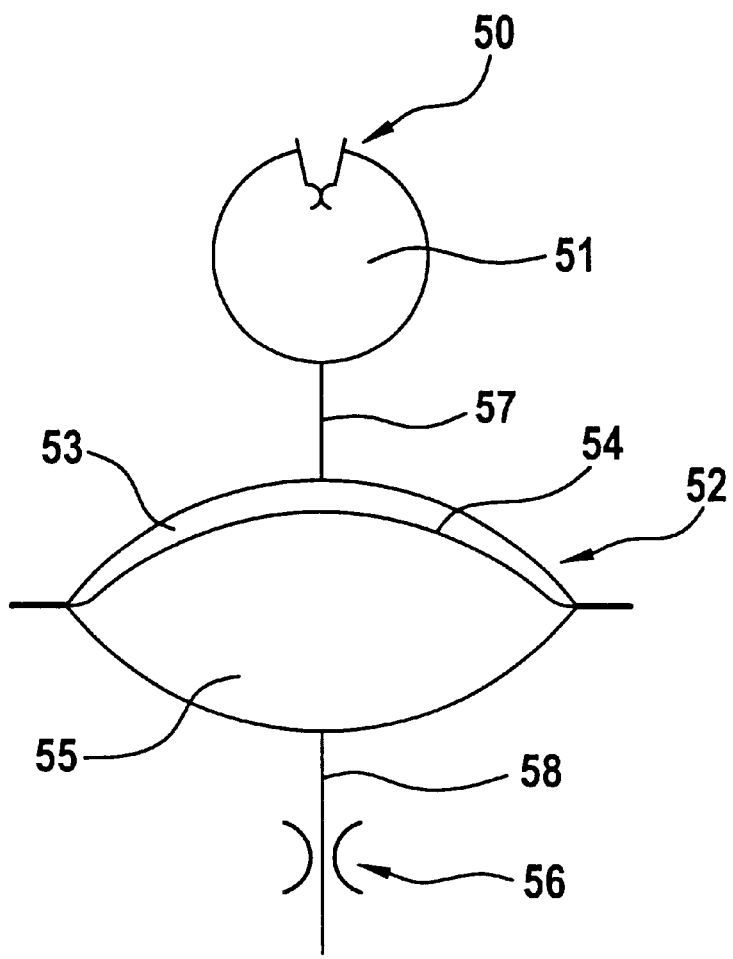
FIG. 4: pressure pump arrangement

FIG. 4 shows a schematic diagram of a pressure pump that can be preferably used in systems according to the present invention. The pressure pump firstly has an inlet valve (50) through which gas pressure can be applied to the pressure container (51) by means of a device e.g. with a plunger. The valve closes after the pipette or pressure connection has been pulled out to maintain gas pressure in the pressure container. A channel (57) connects the pressure container to a membrane system (52) which has a flexible impermeable membrane (54). In the initial stage ready for an application the membrane (54) is in a position such that the hollow space (53) is small or even microscopic and the region (55) filled with perfusion liquid is large. The gas flowing through the channel (57) from the pressure container displaces the membrane and perfusion liquid is squeezed out of the reservoir (55) into the channel (58). A flow restrictor (56) is located downstream of the membrane system for example in the form of a tapering of the channel which limits the amount of liquid emerging from the reservoir (55) per unit of time and keeps it constant. This enables a constant flow of perfusion liquid to be provided for several days in order to supply an exchange region.

The pump arrangement shown in FIG. 4 is particularly advantageous with respect to manufacturing a system according to the present invention with a sandwich structure since the upper half shell of the membrane arrangement be formed as a recess in the first member and the lower half shell can be formed by a recess in the second member and the membrane (54) can be attached in a simple manner between these two half shells or members by clamping or glueing.

What is claimed is:

1. A system for determining the concentration of at least one analyte in a liquid, the system comprising:
   a first member and at least one second member each having a respective surface of which at least one has a recess and the first and second member are joined together so that the at least one recess is at least partially closed by the surface of the other member to form a channel, and at least one of the first and second members contain an exchange region that is formed to take up substances from the liquid,
   a sensor located downstream of the exchange region and formed to determine the concentration of an analyte, and
   wherein the system has at least one integrated reservoir which is connected to the channel.

2. System as claimed in claim 1, wherein at least a part of the channel is located in the exchange region.

3. System as claimed in claim 1, in which the at least one reservoir is formed by a recess in the first or/and the second member.

4. System as claimed in claim 1, which contains a pump for moving liquid through the channel by means of pressure or underpressure.

5. System as claimed in claim 4, in which the pump is integrated into the arrangement comprising the first and second member.

6. System as claimed in claim 1, in which the at least one reservoir or an additional reservoir is used to hold liquid and is located downstream of the sensor.

7. System as claimed in claim 1, which has a restrictor to limit flow in the channel.

8. System as claimed in claim 1, in which the member having the recess contains a plate and a foil with recesses that is attached to the plate such that the recess is formed by interaction of the plate and foil.

9. System as claimed in claim 1, in which all reservoirs necessary for the function of the system are integrated into the first and/or second member.

10. System as claimed in claim 4, in which the pump is integrated into the system.

11. System as claimed in claim 1, wherein the liquid is body fluid and at least a part of the channel can be inserted into the body.

12. A system for determining the presence of an analyte in a body fluid, the system comprising:
   a first member having a first surface,
   a second member having a second surface, at least one of the first and second surfaces including a recess, the second member being joined to the first member so that the recess is at least partially closed by the opposing surface to form a channel,
   an exchange region formed in at least one of the first and second members, the exchange region being in fluid communication with the channel and formed to receive substances from the body fluid therein,
   a reservoir in fluid communication with the channel, and
   an analyte sensor located downstream of the exchange region.

13. The system of claim 12 wherein at least a part of the channel is located in the exchange region.

14. The system of claim 13 wherein at least one of the first and second members includes a plate and a foil and the recess is defined by the plate and the foil.

15. The system of claim 12 wherein the system includes two reservoirs.

16. The system of claim 12 further comprising a pump formed to provide pressure or underpressure to the channel.

17. The system of claim 16 wherein the pump is integrated into the arrangement comprising the first and second member.

18. The system of claim 12 further comprising a waste reservoir located downstream of the sensor.

19. The system of claim 12 wherein the channel is tapered.

20. The system of claim 12 wherein the member having the recess contains a plate and a foil with recesses that is attached to the plate such that the recess is formed by interaction of the plate and foil.

21. A system for determining the presence of an analyte in a body fluid, the system comprising:
   a first member having a first surface and a reservoir having an opening extending through the first surface,
   a second member joined to the first member, the second member having a second surface facing the first surface and extending across the opening, the second surface including a dialysis channel having an inlet and an outlet, a perfusate channel extending from the reservoir to the dialysis channel and being at least partially covered by the first surface, and a dialysate channel extending from the outlet of the dialysis channel, and
   an analyte sensor in communication with the dialysate channel.

22. The system of claim 21 wherein the second member includes a plate and a foil and the dialysis channel is defined by the plate and the foil.

23. The system of claim 21 further comprising a pump formed to provide pressure or underpressure such that liquid is transported from the reservoir through the dialysis channel and to the sensor.

24. The system of claim 21 further comprising a bottom part coupled to the second member and the bottom part is formed to define a waste reservoir downstream of the sensor.

25. The system of claim 21, wherein the second member includes a plate and a foil with recesses that is attached to the plate such that the recess is formed by interaction of the plate and foil.

26. The system of claim 1, wherein the exchange region comprises a membrane.

27. The system of claim 1, wherein the exchange region comprises microperfusion perforations.

28. The system of claim 12, wherein the exchange region comprises a membrane.

29. The system of claim 12, wherein the exchange region comprises microperfusion perforations.

* * * * *